US010105105B2

(12) United States Patent
Hong et al.

(10) Patent No.: US 10,105,105 B2
(45) Date of Patent: Oct. 23, 2018

(54) MOVEMENT PATTERN MEASURING APPARATUS USING EEG AND EMG AND METHOD THEREOF

(71) Applicant: SOONGSIL UNIVERSITY RESEARCH CONSORTIUM TECHNO-PAR, Seoul (KR)

(72) Inventors: Jiman Hong, Seoul (KR); Giwook Kang, Seoul (KR)

(73) Assignee: SOONGSIL UNIVERSITY RESEARCH CONSORTIUM TECHNO-PARK, Seoul (KR)

( * ) Notice: Subject to any disclaimer, the term of this patent is extended or adjusted under 35 U.S.C. 154(b) by 190 days.

(21) Appl. No.: 15/219,294

(22) Filed: Jul. 26, 2016

(65) Prior Publication Data

US 2017/0035313 A1 Feb. 9, 2017

(30) Foreign Application Priority Data

Aug. 3, 2015 (KR) .......................... 10-2015-0109470

(51) Int. Cl.
*A61B 5/00* (2006.01)
*A61B 5/0476* (2006.01)
*A61B 5/0488* (2006.01)
*A61B 5/11* (2006.01)

(52) U.S. Cl.
CPC .......... *A61B 5/7264* (2013.01); *A61B 5/0476* (2013.01); *A61B 5/0488* (2013.01); *A61B 5/1126* (2013.01)

(58) Field of Classification Search
CPC ... A61B 5/7264; A61B 5/0476; A61B 5/0488; A61B 5/1126

USPC ................................................. 600/300, 301
See application file for complete search history.

(56) References Cited

U.S. PATENT DOCUMENTS

2010/0262377 A1* 10/2010 Jensen ................... A61B 5/048
702/19
2012/0197092 A1* 8/2012 Luo ....................... A61B 5/0478
600/301

FOREIGN PATENT DOCUMENTS

KR          10-1293446 B1     8/2013

* cited by examiner

*Primary Examiner* — Michael Carey
(74) *Attorney, Agent, or Firm* — Revolution IP, PLLC

(57) ABSTRACT

Disclosed is an apparatus for measuring movements of a user, which may include: a sample pattern storing unit for storing one or more sample patterns which are obtained by patterning EEG waveforms and EMG values; a communication unit for receiving an EEG waveform and an EMG value of the user measured by the EEG and EMG sensors; a pattern normalizing unit for selecting sample patterns with the highest similarity to the received user's patterns among the stored sample patterns, and for normalizing the received user's patterns so that their amplitudes and periods coincide with those of the selected sample patterns; a movement estimating unit for estimating movement of the user by inputting the normalized EEG waveform and EMG value in an artificial neural network algorithm; and a movement determining unit for calculating the user's movement by applying each weight value of the EEG and EMG to each movement estimation value.

8 Claims, 3 Drawing Sheets

[FIG. 1]
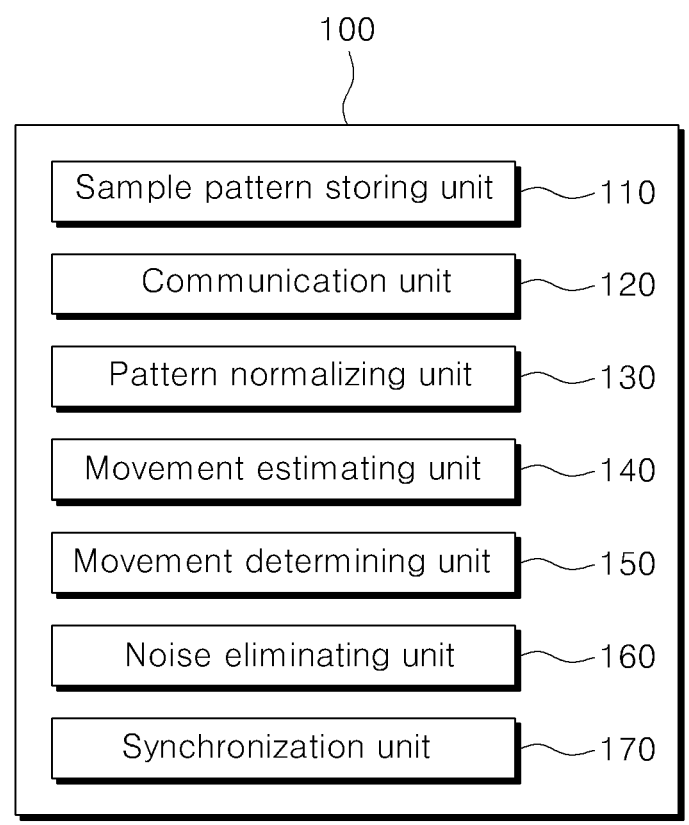

[FIG. 2]
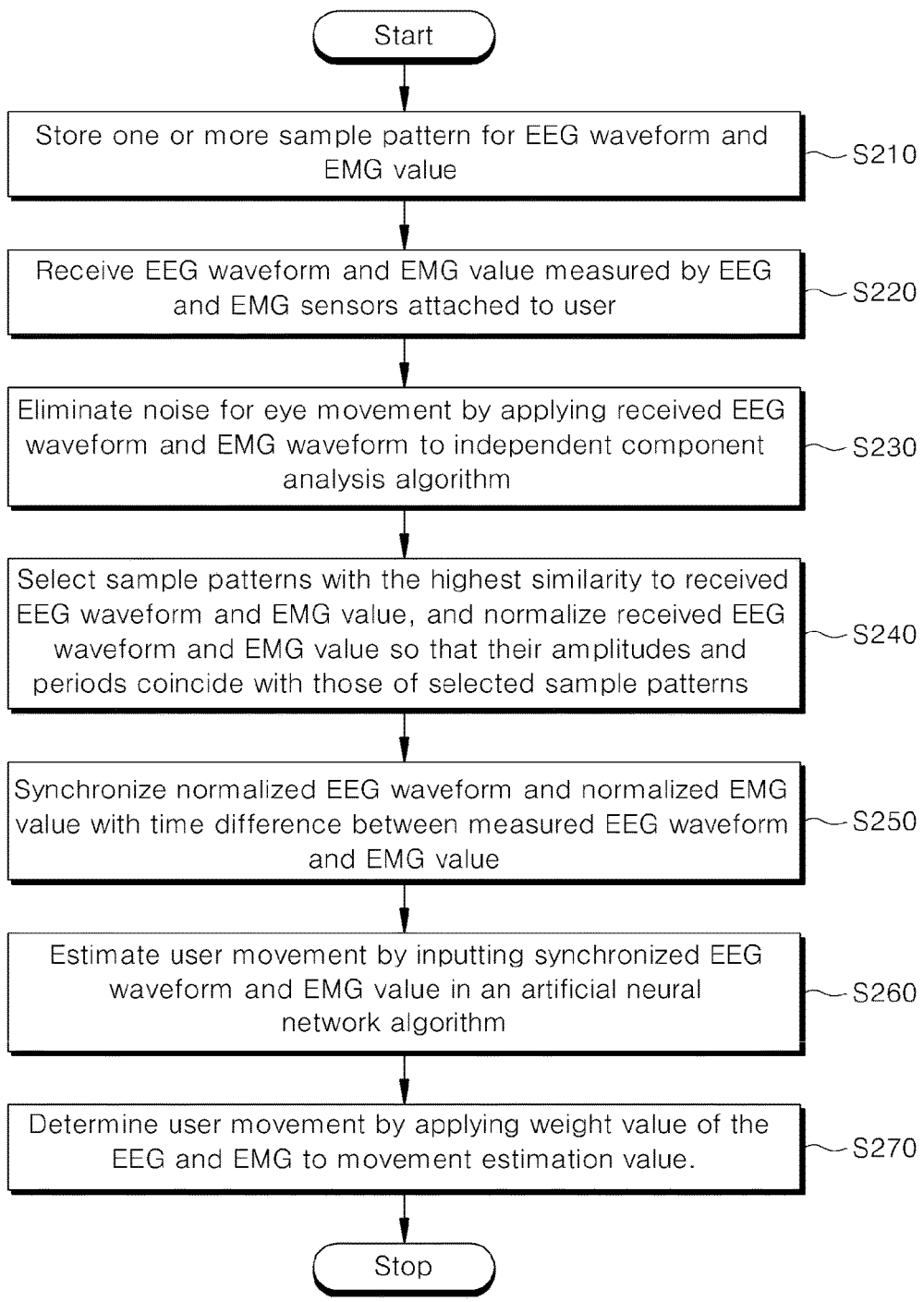

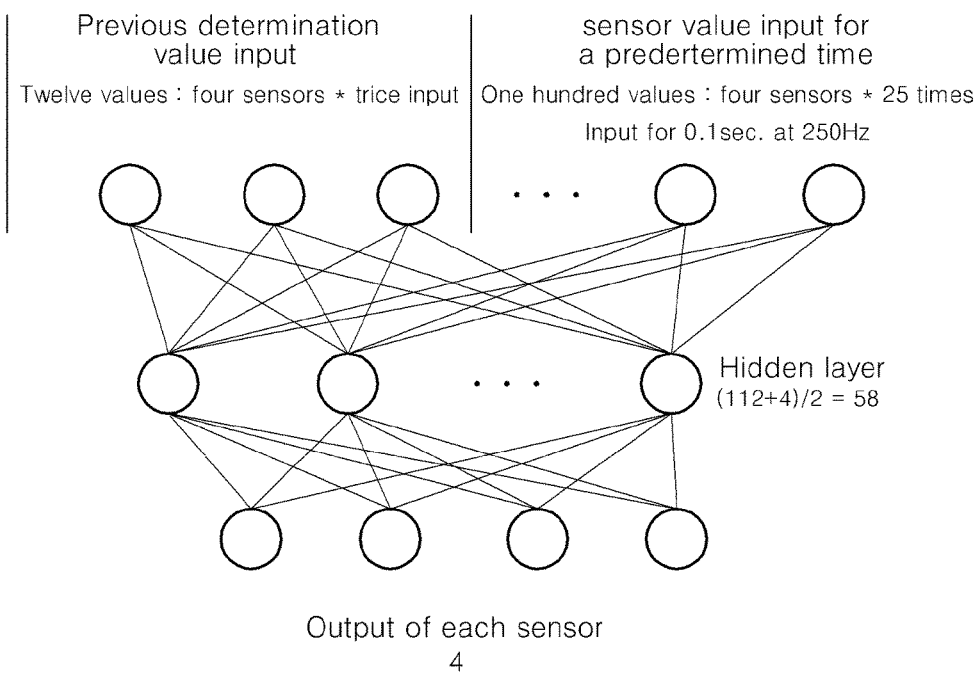
[FIG. 3]

MOVEMENT PATTERN MEASURING APPARATUS USING EEG AND EMG AND METHOD THEREOF

CROSS-REFERENCE TO RELATED APPLICATION

This application claims priority to and the benefit of Korean Patent Application No. 10-2015-0109470 filed in the Korean Intellectual Property Office on Aug. 3, 2015, the entire contents of which are incorporated herein by reference.

BACKGROUND OF THE INVENTION (a) Field of the Invention

The present disclosure relates to a movement pattern measuring apparatus using electroencephalogram (EEG) and electromyogram (EMG) data and a method thereof. More particularly, the present disclosure relates to an apparatus and a method for analyzing user movement patterns by using EEG waveforms and EMG values measured from a user.

(b) Description of the Related Art

Human-Computer Interface (HCI) based bio-signal is a technology which enables the interfaces between human and computers by using bio-signals which can be artificially created, particularly when the elderly and infirm, and the disabled use the computers. Further, this is a technology which creates commands for controlling operation of rehabilitation tools such as a wheelchair, an artificial limb, etc., and can be utilized as the interface for a wearable computer or crippled people.

In HCI, since the bio-signals based on EEG and EMG can be used as input signals without using a keyboard or a touchpad, direct activities for input are not required. Accordingly, in the field of HCI, for disabled people with uncomfortable legs and arms, technologies related with the computer input and the artificial limb have been studied.

Brainwave signals or EEG signals refer to electrical fluctuation created by interactions between neurons in the nervous system, and are measured by electrodes placed on the scalp. These EEG signals may be used for sleep state analysis, concentration or tension degree measurement, schematic feeling recognition, etc.

HCI using the EEG signals is also applied to games. In this case, without any controller or keyboard, only brainwaves are used as inputs of the computer. Currently, researches on a game input technology capable of being most widely used and allowing various inputs have been actively attempted. By using that the concentration degree can be measured via the brainwaves, another research, which utilizes a result obtained from a waveform of a psychiatric patient in the meditation state for a diagnosis, is also being done.

As such, various technologies using the brainwaves serving as a means for HCI have been studied, but there are some problems. Noise and artifacts are inevitably mixed in the measured brainwave, so information loss by the noise and artifacts may occur. These bring a difficulty in analyzing the information.

Since a waveform measured by an EEG sensor when a user performs a specific activity has a simple wavelength, the brainwave corresponding to the specific activity may have one kind of wavelength, but the activity corresponding to one kind of wavelength may be plural. In order to accurately match the measured brainwave with the specific activity, therefore, a technology of measuring EEG and EMG using EEG and EMG sensors together is required.

Further, in known technologies, to pattern the measured brainwave, the most similar pattern of a series of patterns stored in a database was selected. However, because each person's brainwave has different amplitude, such a patterning has a limitation in searching an accurate pattern. Accordingly, after several measurements, a normalization process for the individual brainwaves should be performed.

Korean Patent Publication No. 10-1293446 (published on Aug. 5, 2013) discloses a background technique of the present disclosure.

SUMMARY OF THE INVENTION

The present invention has been made in an effort to provide an apparatus and a method for analyzing user movement patterns by using EEG waveforms and EMG values measured from a user.

To accomplish the objects of the present disclosure, an exemplary embodiment of the present disclosure provides an apparatus for measuring movements of a user by using an electroencephalogram (EEG) sensor and an electromyogram (EMG) sensor, which may include: a sample pattern storing unit for storing one or more sample patterns which are obtained by patterning EEG waveforms and EMG values; a communication unit for receiving an EEG waveform and an EMG value of the user measured by the EEG and EMG sensors; a pattern normalizing unit for selecting sample patterns with the highest similarity to the received user's EEG waveform and EMG value among the stored sample patterns, and for normalizing the received EEG waveform and EMG value so that their amplitudes and periods coincide with those of the selected sample patterns; a movement estimating unit for estimating movement of the user by inputting the normalized EEG waveform and EMG value in an artificial neural network algorithm; and a movement determining unit for calculating the user's movement by applying each weight value of the EEG and EMG to each movement estimation value.

The apparatus may further include: a noise eliminating unit for eliminating noise for eye movement by applying the EEG waveform and EMG value, received from the EEG sensor and EMG sensor, to an independent component analysis algorithm; and a synchronization unit for synchronizing the normalized EEG waveform and the normalized EMG value by using a time difference between the EEG waveform and EMG value measured by the EEG sensor and EMG sensor.

The pattern normalizing unit may normalize the noise-eliminated EEG waveform and EMG value by using normalization ratios which are set with control ratios used for controlling the amplitudes and periods of the noise-eliminated EEG waveform and EMG value to coincide with those of the selected sample patterns or which are set by being externally inputted.

The movement estimating unit may estimate the user's movement by using the synchronized EEG waveform and EMG value at the current time, the synchronized EEG waveform and EMG value at time prior to the current time, and a movement estimation value outputted through the artificial neural network at time prior to the current time, as input values of the artificial neural network algorithm.

The sample pattern storing unit may pattern the normalized EEG waveform and EEG value, and a movement estimation value outputted from the artificial neural network algorithm, and may store them as one sample pattern.

The movement determining unit ma set a movement estimation value depending on the EMG values to have the weight value larger than that of a movement estimation value depending on the EEG waveforms.

Another exemplary embodiment of the present disclosure provides a movement pattern measuring method using a movement pattern measuring apparatus, which may include: storing one or more sample patterns which are obtained by patterning EEG waveforms and EMG values; receiving an EEG waveform and an EMG value measured by an EEG sensor and an EMG sensor attached to a user; selecting sample patterns with the highest similarity to the received user's EEG waveform and EMG value among the stored sample patterns, and normalizing the received EEG waveform and EMG value so that their amplitudes and periods coincide with those of the selected sample patterns; estimating movement of the user by inputting the normalized EEG waveform and EMG value in an artificial neural network algorithm; and determining the user's movement by applying each weight value of the EEG and EMG to each movement estimation value.

According to the present disclosure, since the movement of the current user is estimated and determined with the measured EEG waveform and EMG value at the current time, the EEG waveform and EMG value measured at time prior to at the current time, and the movement estimation value at time prior to at the current time, more accurate movement determination becomes possible.

Further, the normalization for each person can be adequately performed by utilizing data measured from each person. Furthermore, by utilizing the EEG and EMG sensors together, the present disclosure can more accurately determine the user's movement even with a small number of sensors compared with conventional technologies. Accordingly, the cost of normalization for each person, and the cost of sensors can be reduced.

BRIEF DESCRIPTION OF THE DRAWINGS

FIG. 1 is a schematic view of a movement pattern measuring apparatus according to an exemplary embodiment of the present disclosure.

FIG. 2 is a flow chart illustrating a movement pattern measuring method according to the exemplary embodiment of the present disclosure.

FIG. 3 exemplarily illustrates scheme of an artificial neural network algorithm of the movement pattern measuring apparatus according to the exemplary embodiment of the present disclosure.

DETAILED DESCRIPTION OF THE INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive, and like reference numerals designate like elements throughout the specification.

In addition, unless explicitly described to the contrary, the word "comprise" and variations such as "comprises" or "comprising" will be understood to imply the inclusion of stated elements, but not the exclusion of any other elements.

The present disclosure relates to a movement pattern measuring apparatus using electroencephalogram (EEG) and electromyogram (EMG) data, and provides a method allowing a user's movement to be more accurately determined with EEG waveforms and EMG values measured by EEG and EMG sensors.

In an exemplary embodiment of the present disclosure, two EEG sensors and two EMG sensors are used. The two EEG sensors are placed on the frontal lobe, and the two EMG sensors are placed on specific body parts desired to be measured. The movement pattern measuring apparatus receives EEG and EMG data measured by the sensors attached to the user's body, eliminates noise from the received data by using an independent component analysis algorithm, normalizes the data, and then determines the user's movement through an artificial neural network algorithm. Since the determined movement value and measured data are stored and utilized again, normalization for each person is possible and the user's movement can be more accurately determined.

Hereinafter, the movement pattern measuring apparatus according to the exemplary embodiment of the present disclosure will be described in detail with reference to the accompanying drawings.

FIG. 1 is a schematic view of a movement pattern measuring apparatus according to an exemplary embodiment of the present disclosure.

The movement pattern measuring apparatus 100 includes a sample pattern storing unit 110, a communication unit 120, a pattern normalizing unit 130, and a movement estimating unit 140, and a movement determining unit 150. The movement pattern measuring apparatus 100 may further include a noise eliminating unit 160 and a synchronization unit 170.

The sample pattern storing unit 110 stores one or more sample patterns for electroencephalogram (EEG) waveforms and electromyogram (EMG) values. The sample pattern storing unit 110 has already stored a sample pattern which is obtained by patterning the amplitude of an EEG waveform, or an EMG value for a specific movement, but may further store another sample pattern which is obtained by patterning a newly measured EEG waveform or EMG value.

The communication unit 120 receives an EEG waveform and EMG value of a user, measured by an EEG sensor and an EMG sensor.

The communication unit 120 may receive the EEG waveform and the EMG value measured by the EEG sensor and the EMG sensor through a wired network or a wireless network. Examples of the wireless network are short-range communications including ZIGBEE, BLUETOOTH, NFC (near field communication), etc., and long-range communications including 3G, 4G, LTE, and LTE-A, but the present disclosure is not necessarily limited thereto.

The pattern normalizing unit 130 receives the EEG waveform and EMG value from the communication unit 120 or the noise eliminating unit 160, selects sample patterns with the highest similarity to the received user's EEG waveform and EMG value among the stored sample patterns, and normalizes the received EEG waveform and EMG value so that their amplitudes and periods coincide with those of the selected sample patterns.

The movement estimating unit 140 estimates movement of the user by inputting the normalized EEG waveform and EMG value in an artificial neural network algorithm.

Here, the artificial neural network refers to the entire models of networks, in which artificial neurons or nodes, which form a network through connections between synapses, have problem-solving ability by varying the strength of connection between the synapses through learning. The process of estimating the user's movement using this artificial neural network will be described later in further detail.

The movement determining unit 150 calculates the user's movement by applying each weight value of the EEG and EMG to each movement estimation value.

The noise eliminating unit 160 eliminates noise for eye movement by applying the EEG waveform and EMG value, received from the EEG sensor and EMG sensor, to an independent component analysis algorithm. Here, the independent component analysis algorithm is a computational method for separating a multivariate signal into additive subcomponents. Particularly, the independent component analysis is a special case of blind signal separation.

The synchronization unit 170 synchronizes the normalized EEG waveform and the normalized EMG value by using a time difference between the received EEG waveform and EMG value.

When the user attempts a specific movement, a brain signal is first created, and the movement is performed in response to the created brain signal. That is, the EEG waveform is measured in advance of the EMG value. For this reason, the synchronization unit 170 first calculates the time difference between the received EEG waveform and EMG value, and synchronizes the time of the normalized EEG waveform and the normalized EMG value by using the calculated time difference so that both can represent the same movement.

Hereinafter, a method for measuring the user's movement using the movement pattern measuring apparatus according to the exemplary embodiment of the present disclosure is described in detail with reference to FIG. 2 and FIG. 3.

FIG. 2 is a flow chart illustrating a movement pattern measuring method according to the exemplary embodiment of the present disclosure, and FIG. 3 exemplarily illustrates scheme of an artificial neural network algorithm of the movement pattern measuring apparatus according to the exemplary embodiment of the present disclosure.

First, at step S210, the movement pattern measuring apparatus 100 stores one or more sample patterns which are obtained by patterning EEG waveforms and EMG values. The sample patterns refer to standard EEG waveforms and EMG values of the ordinary persons, and movements corresponding to those EEG waveforms and EMG values, all of which are previously recorded and stored.

In addition, in the case in which the user's movement has been determined with the EEG waveform and EMG value measured from the user, the movement pattern measuring apparatus 100 may store another sample pattern obtained by patterning the EEG waveform and EMG value used for determining the user's movement, and the determined movement value.

Next, at step S220, the movement pattern measuring apparatus 100 receives an EEG waveform and an EMG value, each measured by the EEG sensor and EMG sensor which are attached to the user.

The movement pattern measuring apparatus 100 may receive EEG waveforms and EMG values in real time or at certain time intervals, communicating with the EEG sensor and EMG sensor.

The EEG sensor and EMG sensor are connected to the movement pattern measuring apparatus 100 by wires so that the measured EEG waveform and EMG value can be communicated thereto. However, they may be wirelessly connected to the movement pattern measuring apparatus 100.

Examples of wireless network are short-range communications including ZIGBEE, BLUETOOTH, NFC (near field communication), etc., and long-range communications including 3G, 4G, LTE, and LTE-A, but the present disclosure is not necessarily limited thereto.

Next, at step S230, the movement pattern measuring apparatus 100 eliminates noise for eye movement by applying the EEG waveform and EMG value, received from the EEG sensor and EMG sensor, to an independent component analysis algorithm.

There is a higher possibility of generating noise and artifact in the EEG waveform and the EMG value measured by the EEG sensor and EMG sensor. In this case, to obtain an accurate measurement value, the noise and artifact should be removed. The movement pattern measuring apparatus 100 can eliminate EEG signals for the eye movement from the measured EEG waveforms by applying them to the independent component analysis algorithm. That is, the noise can be efficiently eliminated because the EEG signals are separated to be source signals which are maximally independent and minimally dependent by the independent component analysis algorithm.

In addition, the movement pattern measuring apparatus 100 may also eliminate any noise and artifact with no causal relationship to the user's movement as well as the noise for the eye moment. For example, in the case in which the user has tic disorder which may have an influence on the EEG waveform and the EMG value, the movement pattern measuring apparatus 100 can eliminate the corresponding noise and artifact from the measured EEG waveform and the EMG value.

Next, at step S240, the movement pattern measuring apparatus 100 selects sample patterns with the highest similarity to the EEG waveform and EMG value which the noise and artifact have been removed from, and normalizes the EEG waveform and EMG value so that their amplitudes and periods coincide with those of the selected sample patterns.

In detail, the movement pattern measuring apparatus 100 analyzes features of the received EEG waveform and EMG value, and selects two sample patterns which are determined to be most similar to the features of the received EEG waveform and EMG value. Since each person has a different EEG waveform and EMG value, to accurately determine the user's movement, the movement pattern measuring apparatus 100 normalizes the received EEG waveform and EMG value so that their amplitudes and periods coincide with those of the selected sample patterns.

In such a normalization process, the movement pattern measuring apparatus 100 stores control ratios in an additional storage device, and may use the stored control ratios when the EEG waveform and EMG value, which are measured after storing the normalization ratios, are normalized.

That is, the movement pattern measuring apparatus 100 may normalizes the noise-eliminated EEG waveform and EMG value by using normalization ratios which are set with control ratios used for controlling the amplitudes and periods of the noise-eliminated EEG waveform and EMG value to coincide with those of the selected sample patterns or which are set by being externally inputted.

Here, the most frequently stored ratio of the stored ratios during N (N is a natural number) normalization processes are performed may be set as the normalization ratio by the movement pattern measuring apparatus 100. In the normalization process performed after the normalization ratio has been set, the set normalization ratio is first applied to this process, and if the ratio is inadequate, the amplitudes and periods of the EEG waveform and EMG value may be controlled again for the normalization.

Then, at step S250, the movement pattern measuring apparatus 100 synchronizes the normalized EEG waveform and the normalized EMG value by using the time difference between the measured EEG waveform and the EMG value.

Even if the movement pattern measuring apparatus 100 receives the EEG waveforms and EMG values from the EEG sensor and EMG sensor in real time or at certain time intervals, the EEG waveform and EMG value, both representing the same movement, are measured at different time points. Accordingly, the movement pattern measuring apparatus 100 synchronizes the EEG waveform and EMG value for the same movement by controlling the time difference therebetween based on either of them.

For example, in the case when the user to which the EEG and EMG sensors are attached attempts a specific movement, the movement pattern measuring apparatus 100 may calculate the time difference between a time point of creating an EEG waveform in response to a brain signal for the specific movement and a time point of creating an EMG value of moving muscles by the brain signal, or may receives the time difference from the user, and then synchronizes the two time points by using the calculated or received time difference.

Next, at step S260, the movement pattern measuring apparatus 100 estimates the user's movement by inputting the normalized EEG waveform and EMG value in the artificial neural network.

In addition, the movement pattern measuring apparatus 100 may estimate the user's movement by using the synchronized EEG waveform and EMG value at the current time, the synchronized EEG waveform and EMG value at time prior to the current time, and a movement estimation value outputted through the artificial neural network at time prior to the current time, as input values of the artificial neural network algorithm.

In FIG. 3, the artificial neural network algorithm is configured by an input layer, at least one intermediate hidden layer, and an output layer.

On the assumption that the user's movement is in a flow having the context, the movement pattern measuring apparatus 100 may use all of the sensor values synchronized at the current time and at time prior to the current time, and the movement estimation value outputted at time prior to the current time, as input values of the artificial neural network algorithm.

As described above, two EEG sensors and two EMG sensors are used in the present disclosure. Accordingly, values recorded by four sensors may be used as inputs of the artificial neural network algorithm.

As shown in FIG. 3, the movement pattern measuring apparatus 100 according to the exemplary embodiment of the present disclosure uses a three-layered model as a scheme of the artificial neural network algorithm. However, the present disclosure is not necessarily limited thereto. Each circular node represents an artificial neuron with problem-solving ability by varying the strength of connection between the synapses through learning.

In an example shown in FIG. 3, the input layer of the artificial neural network inputs twelve normalized sensor values, which are resulted from three normalization processes for the two EEG sensors and two EMG sensors at time prior to the current time, as previous determination values, measures the sensor values for a predetermined time (for example, 0.1 sec. based on 250 Hz), and inputs the synchronized sensor values. In the exemplary embodiment of the present disclosure, an intermediate value of the input nodes and output nodes is 58, but it is not necessarily limited thereto. The movement pattern measuring apparatus 100 forms enough nodes at the intermediate hidden layer, and outputs each movement estimation value for the respective four sensors.

When a new user to which the sensors are attached uses the movement pattern measuring apparatus 100 for the first time, the movement pattern measuring apparatus 100 may estimate the user's movement by using the nodes previously trained with the sample values. When the normalization of EEG waveform and EMG value has been completed and a predetermined amount of information about the corresponding user has been accumulated, the movement pattern measuring apparatus 100 trains the nodes with the previous determination values, and includes a recent determination value in the input in order to estimate the user's movement more accurately.

Next, at step S270, the movement pattern measuring apparatus 100 determines the user's movement by applying the weight values of EEG waveform and the EMG value to the estimated user's movement.

In detail, the movement pattern measuring apparatus 100 finally determines the user's movement by respectively applying the weight value of EEG waveform and the weight value of the EMG value to the movement estimation value depending on the EEG waveforms measured by two EEG sensors, and to the movement estimation value depending on the EMG values measured by two EMG sensors.

In this case, the movement estimation value depending on the EMG values may have the weight value larger than that of the movement estimation value depending on the EEG waveforms. This is why the EMG value measured from actually moving muscles has higher accuracy and comparatively less noise and artifact than the EEG signal for commanding the movement. For this reason, the movement pattern measuring apparatus 100 may set the weight value of the EMG value to be larger than that of the EEG waveform.

As such, when the user's movement has been determined with the measured EEG waveforms and EMG values, the normalized EEG waveform or EEG value for the determined movement, and the movement estimation value outputted from the artificial neural network algorithm are patterned and stored as one sample pattern.

That is, the movement pattern measuring apparatus 100 stores the measured input value, estimated input value, and resultant value again as one sample pattern, and may utilize this sample pattern at the steps S240 and S260.

According to the exemplary embodiment of the present disclosure, since the movement of the current user is estimated and determined with the measured EEG waveform and EMG value at the current time, the EEG waveform and EMG value measured at time prior to at the current time, and the movement estimation value at time prior to at the current time, more accurate movement determination becomes possible.

Further, the normalization for each person can be adequately performed by utilizing data measured from each person. Furthermore, by utilizing the EEG and EMG sensors together, the present disclosure can more accurately determine the user's movement even with a small number of sensors compared with conventional technologies. Accordingly, the cost of normalization for each person, and the cost of sensors can be reduced.

Example embodiments have been disclosed herein and although specific terms are employed, they are used and are to be interpreted in a generic and descriptive sense only and not for purpose of limitation. In some examples, as would be apparent to one of ordinary skill in the art as of the filing of the present application, features, characteristics and/or elements described in connection with a particular embodiment may be used singly or in combination with features, characteristics and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An apparatus for measuring movements of a user by using an electroencephalogram (EEG) sensor and an electromyogram (EMG) sensor, which comprising:
a sample pattern storing unit for storing one or more sample patterns which are obtained by patterning EEG waveforms and EMG values; a communication unit for receiving an EEG waveform and an EMG value of the user measured by the EEG and EMG sensors;
a pattern normalizing unit for selecting sample patterns with the highest similarity to the received user's EEG waveform and EMG value among the stored sample patterns, and for normalizing the received EEG waveform and EMG value so that their amplitudes and periods coincide with those of the selected sample patterns; a movement estimating unit for estimating movement of the user by inputting the normalized EEG waveform and EMG value in an artificial neural network algorithm;
a movement determining unit for determining the user's movement by applying a weight value of respective one of the EEG and EMG to each movement estimation value;
a noise eliminating unit for eliminating noise for eye movement by applying the EEG waveform and EMG value, received from the EEG sensor and EMG sensor, to an independent component analysis algorithm; and
a synchronization unit for synchronizing the normalized EEG waveform and the normalized EMG value with a time difference between the EEG waveform and EMG value measured by the EEG sensor and EMG sensor, wherein
the pattern normalizing unit normalizes the noise-eliminated EEG waveform and EMG value by using normalization ratios which are set with control ratios used for controlling the amplitudes and periods of the noise-eliminated EEG waveform and EMG value to coincide with those of the selected sample patterns or which are set by being externally inputted.

2. The apparatus of claim 1, wherein the movement estimating unit estimates the user's movement by using the synchronized EEG waveform and EMG value at the current time, the synchronized EEG waveform and EMG value at time prior to the current time, and a movement estimation value outputted through the artificial neural network at a time prior to the current time, as input values of the artificial neural network algorithm.

3. The apparatus of claim 2, wherein the sample pattern storing unit patterns the normalized EEG waveform and EEG value, and a movement estimation value outputted from the artificial neural network algorithm, and then stores them as one sample pattern.

4. The apparatus of claim 1, wherein the movement determining unit sets a movement estimation value depending on the EMG values to have a weight value larger than that of a movement estimation value depending on the EEG waveforms.

5. A computer-implemented movement pattern measuring method using a movement pattern measuring apparatus which includes at least one of units being configured and executed by a controller using algorithm associated with least one non-transitory storage device for controlling the movement pattern measuring apparatus, the method, comprising:
storing one or more sample patterns which are obtained by patterning EEG waveforms and EMG values;
receiving an EEG waveform and an EMG value measured by an EEG sensor and an EMG sensor attached to a user;
selecting sample patterns with the highest similarity to the received user's EEG waveform and EMG value among the stored sample patterns, and normalizing the received EEG waveform and EMG value so that their amplitudes and periods coincide with those of the selected sample patterns;
estimating movement of the user by inputting the normalized EEG waveform and EMG value in an artificial neural network algorithm;
determining the user's movement by applying a weight value of respective one of the EEG and EMG to each movement estimation value;
eliminating noise for eye movement by applying the EEG waveform and EMG value, received from the EEG sensor and EMG sensor, to an independent component analysis algorithm; and
synchronizing the normalized EEG waveform and the normalized EMG value by using a time difference between the EEG waveform and EMG value measured by the EEG sensor and EMG sensor, wherein
the normalizing of the received EEG waveform and EMG value includes normalizing the noise-eliminated EEG waveform and EMG value by using normalization ratios which are set with control ratios used for controlling the amplitudes and periods of the noise-eliminated EEG waveform and EMG value to coincide with those of the selected sample patterns or which are set by being externally inputted.

6. The method of claim 5, wherein the estimating of the user's movement includes estimating the user's movement by using the synchronized EEG waveform and EMG value at the current time, the synchronized EEG waveform and EMG value at time prior to the current time, and a movement estimation value outputted through the artificial neural network at a time prior to the current time, as input values of the artificial neural network algorithm.

7. The method of claim 6, wherein the storing of one or more sample patterns includes patterning the normalized EEG waveform and EEG value, and a movement estimation value outputted from the artificial neural network algorithm, and storing them as one sample pattern.

8. The method of claim 5, wherein the determining of the user's movement includes setting a movement estimation value depending on the EMG values to have a weight value larger than that of a movement estimation value depending on the EEG waveforms.

* * * * *